United States Patent
Cobianu et al.

(10) Patent No.: US 10,527,598 B2
(45) Date of Patent: Jan. 7, 2020

(54) METAL OXIDE NANOCOMPOSITE HETEROSTRUCTURE METHODS AND HYDROGEN SULFIDE SENSORS INCLUDING THE SAME

(71) Applicant: HONEYWELL ROMANIA S. R. L., Morris Plains, NJ (US)

(72) Inventors: Cornel P. Cobianu, Bucharest (RO); Viorel Georgel Dumitru, Prahova (RO); Bogdan-Catalin Serban, Bucharest (RO); Alisa Stratulat, Bucharest (RO); Mihai Brezeanu, Bucharest (RO); Octavian Buiu, Bucharest (RO)

(73) Assignee: HONEYWELL ROMANIA S.R.L., Bucharest (RO)

( * ) Notice: Subject to any disclaimer, the term of this patent is extended or adjusted under 35 U.S.C. 154(b) by 0 days.

(21) Appl. No.: 16/059,411

(22) Filed: Aug. 9, 2018

(65) Prior Publication Data
US 2018/0348185 A1   Dec. 6, 2018

Related U.S. Application Data

(62) Division of application No. 14/791,762, filed on Jul. 6, 2015, now Pat. No. 10,067,107.

(30) Foreign Application Priority Data

Jul. 9, 2014   (EP) .................................... 14176418

(51) Int. Cl.
*H01B 1/08*   (2006.01)
*G01N 33/00*   (2006.01)
*G01N 27/12*   (2006.01)

(52) U.S. Cl.
CPC ....... *G01N 33/0044* (2013.01); *G01N 27/127* (2013.01); *H01B 1/08* (2013.01)

(58) Field of Classification Search
CPC ..... G01N 33/0044; G01N 27/127; H01B 1/08
See application file for complete search history.

(56) References Cited

U.S. PATENT DOCUMENTS

| | | | |
|---|---|---|---|
| 2013/0219988 A1 | 8/2013 | Dutta et al. | |
| 2015/0300980 A1 | 10/2015 | Kim et al. | |
| 2016/0005599 A1 | 1/2016 | Lee et al. | |

FOREIGN PATENT DOCUMENTS

| | | | |
|---|---|---|---|
| CN | 103257158 A | * | 8/2013 |
| CN | 103257158 A | | 8/2013 |

(Continued)

OTHER PUBLICATIONS

Choudhary et al. "Selective detection of hydrogen sulfide using copper oxide-doped tin oxide based thick film sensor array". Materials Chemistry and Physics 142 (2013) 370-380. Accepted Jul. 19, 2013. Total pp. 11. (Year: 2013).*

(Continued)

*Primary Examiner* — Mark Kopec
*Assistant Examiner* — Jaison P Thomas
(74) *Attorney, Agent, or Firm* — Alston & Bird LLP

(57) ABSTRACT

A metal oxide heterostructure includes mixing a first precursor and a second precursor to form a precursor aqueous mixture, adding at least one constituent to the precursor aqueous mixture to form a first solution, adding a nanostructuring reagent to the first solution to form a second solution, sonochemically treating the second solution to provide a metal oxide powder, filtering, washing, and drying the metal oxide powder to provide a metal oxide nanocomposite heterostructure for a sensing layer of a hydrogen sulfide sensor. A method for forming a hydrogen sulfide sensor includes the metal oxide heterostructure, forming a sensing (Continued)

material, contacting the sensing material with interdigitated electrodes to form a sensing layer, and thermally consolidating the sensing layer to form the hydrogen sulfide sensor.

12 Claims, 4 Drawing Sheets

(56) References Cited

FOREIGN PATENT DOCUMENTS

| | | |
|---|---|---|
| CN | 103776870 A | 5/2014 |
| KR | 10-2014-0018573 A | 2/2014 |

OTHER PUBLICATIONS

Wang, Tie-Shi, et al., "Synthesis and enhanced H2S gas sensing properties of (Alpha)-MoO3/CuO p-n junction nanocomposite", Sensors and Actuators B: Chemical, vol. 171-172, (2012), 256-262.

Geng, Jun, et al., "Crystal formation and growth mechanism of inorganic nanomaterials in sonochemical syntheses", Science China Chemistry, 55(11), (2012), 2292-2310.

European Application Serial No. 14176418.3, Response filed Sep. 30, 2015 to Extended European Search Report dated Jan. 09, 2015, Jan. 9, 2015, 1-15.

Choudhary, Meenakshi, et al., "Selective detection of hydrogen sulfide using copper oxide-doped tin oxide based thick film sensor array", Materials Chemistry and Physics, 142(1), (Oct. 2013), 370-380.

"European Application Serial No. 14176418.3, Extended European Search Report dated Jan. 9, 2015", 9 pgs.

\* cited by examiner

METAL OXIDE NANOCOMPOSITE HETEROSTRUCTURE METHODS AND HYDROGEN SULFIDE SENSORS INCLUDING THE SAME

RELATED APPLICATIONS

This application is a divisional of U.S. application Ser. No. 14/791,762, filed Jul. 6, 2015, which claims priority under 35 U.S.C. Section 119 to European Patent Application Serial No. 14176418.3, filed on Jul. 9, 2014. The entire contents of both U.S. application Ser. No. 14/791,762 and European Patent Application Serial No. 14176418.3 are incorporated herein by reference.

BACKGROUND

Hydrogen sulfide sensors can be used in various industries to detect hydrogen sulfide, a toxic, flammable, and corrosive gas. For example, hydrogen sulfide sensors can be used for detecting hydrogen sulfide in the petrochemical industry.

SUMMARY

A method of forming a nanocomposite powder of metal oxide heterostructure can include mixing a first precursor and a second precursor to form a precursor aqueous mixture. At least one constituent can be added to the precursor aqueous mixture to form a first solution. A nanostructuring reagent can be added to the first solution to form a second solution. The second solution can be sonochemically treated to provide a nanocomposite powder made of p-type and n-type metal oxides, filtering, washing and drying the metal oxide heterostructure powder. Mixing the metal oxide powder with a binder can provide a solution (slurry) of metal oxide nanocomposite heterostructure to be used for depositing a sensing layer of a hydrogen sulfide sensor.

In an example, a method for forming a hydrogen sulfide sensor includes obtaining, from a batch sonochemical synthesis, the metal oxide heterostructure powder, forming a sensing material slurry, contacting the sensing material with interdigitated electrodes to form a sensing layer, and thermally consolidating the sensing layer to form the hydrogen sulfide sensor.

DETAILED DESCRIPTION OF THE DRAWINGS

The embodiments of the present disclosure will be described, by way of example only, by reference to the FIGS. 1-4 of the accompanying drawing in which.

DETAILED DESCRIPTION

The following Detailed Description is merely exemplary in nature and is not intended to limit the subject matter or the application and uses of the same. Furthermore, there is no intention to be bound by any theory presented in the preceding background or the following detailed description.

Figure 1:
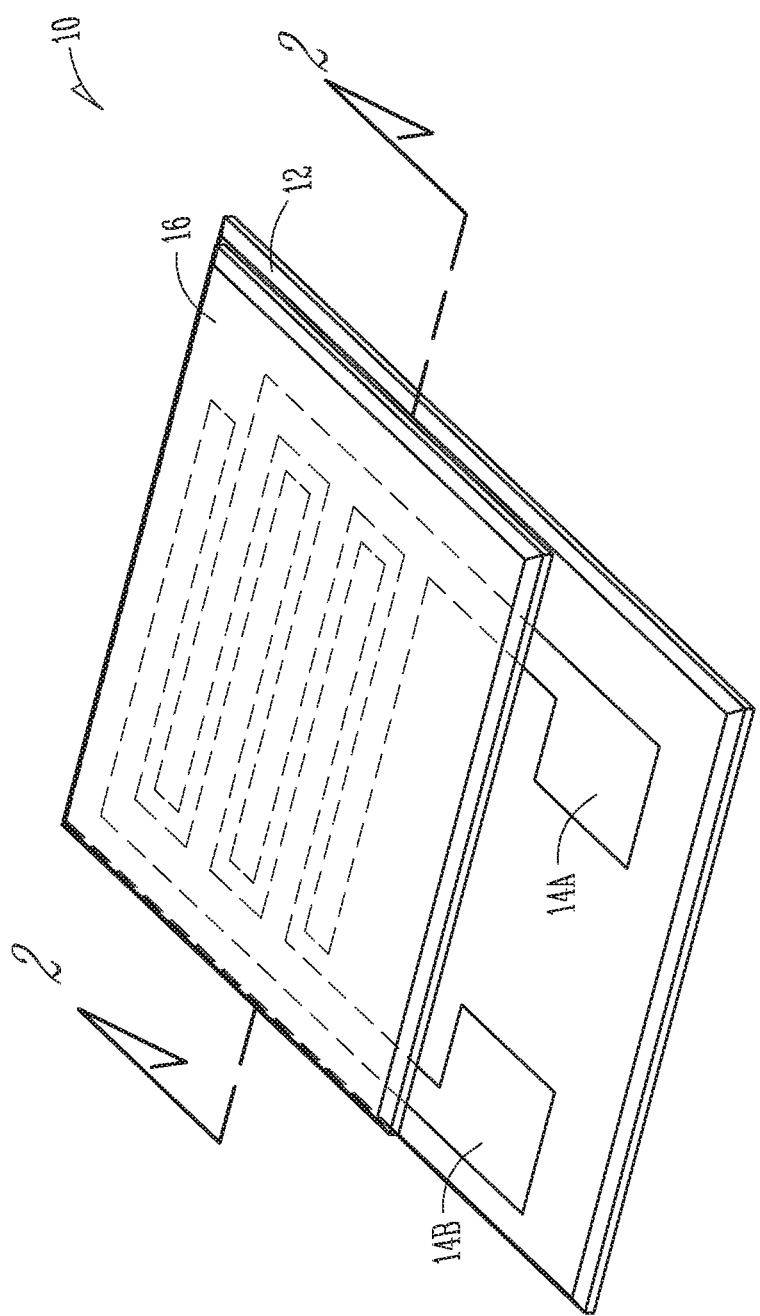
FIG. 1 shows a partial cut-away perspective view of a hydrogen sulfide sensor, in accordance with at least one example.

FIG. 1 shows a partial cut-away perspective view of a hydrogen sulfide sensor 10 (hereinafter also referred to as "sensor 10"), in accordance with at least one example. The sensor 10 can include a substrate 12. The substrate 12 can include at least one of silicon dioxide, silicon, quartz, glass, or the like. In an example, the substrate 12 can be formed of a flexible material such that the substrate 12 can conform to non-planar surfaces. In another example, the substrate 12 is not flexible. Examples of the present hydrogen sulfide sensor 10 based on nanocomposites of metal oxide heterostructures can provide higher sensitivity, such as up to about ten times the hydrogen sulfide sensitivity with respect to hydrogen sulfide sensors based on micro-structured composites. The hydrogen sulfide sensor 10 can be formed by a batch method. In addition, the composite metal oxide nanostructuring can decrease an operating temperature of the sensor, such as from about 300° C. to about 200° C. Further, the decrease in operating temperature can reduce the electric power consumption of the sensor by about 30% as compared to a hydrogen sulfide sensor of the same geometry but without the composite metal oxide nanostructuring.

As shown in the example of FIG. 1, the sensor 10 can include interdigitated electrodes (IDEs) 14A, 14B supported by the substrate 12. The IDEs can be supported by the substrate such as by depositing the IDEs on a surface of the substrate. Interdigitated electrodes 14A, 14B include two individually addressable interdigitated comb-like electrode structures. The IDEs 14A, 14B can include platinum/titanium, gold/chromium, gold/nickel silver, or the like. In an example, the IDEs 14A, 14B can be screen printed on the substrate 12.

As shown in FIG. 1, the sensing layer 16 is configured to interact with hydrogen sulfide. That is, the sensing layer 16 can be in electrical contact with the IDEs 14A, 14B, such that conductivity of the sensor 10 can vary based on the interaction between the sensing layer 16 and the IDEs 14A, 14B when in the presence of varying concentrations of hydrogen sulfide. As discussed herein, the sensing layer 16 can include a metal oxide heterostructure nanocomposite, such as obtained from a batch sonochemical synthesis process described herein. As used herein, a heterostructure includes a p-type-n-type metal oxide structure. Examples, of metal oxide heterostructure nanocomposites include, but are not limited to, multiple component metal oxides including n-type metal oxide semiconductors and p-type metal oxide semiconductors. The n-type metal oxide semiconductors and p-type metal oxide semiconductors can, in various examples, be singular component metal oxides or doped metal oxides (e.g. Fe-doped $MoO_3$, Ce-doped $SnO_2$, In-doped $SnO_2$, Sr-doped $SnO_2$). Examples of n-type metal oxide semiconductors include, but are not limited to, $SnO_2$, Ce-doped $SnO_2$, ZnO, $MoO_3$, $V_2O_5$, V-doped $WO_3$, and the like. Examples, of p-type metal oxide semiconductors include, but are not limited to, CuO, $Cr_2O_3$, NiO, Mg-doped ZnO, N-doped ZnO, In-doped ZnO, Li-doped NiO, $CuAlO_2$, $Cu_2SrO_2$, and $CuGaO_2$, and the like. Examples of multiple component metal oxides include, but are not limited to, $MoO_3$—CuO, $SnO_2$—CuO, and ZnO—CuO, $SnO_2$—NiO, $SnO_2$—$Cr_2O_3$, ZnO—NiO, ZnO—$Cr_2O_3$, $MoO_3$—NiO, and the like.

In the absence of hydrogen sulfide the electrical resistance of the interaction between the sensing layer 16 and the IDEs 14A, 14B is high due to the relatively high barrier height at the interfaces between the n-type and p-type within the metal oxide heterostructure. In the presence of hydrogen sulfide, the p-type metal oxide reacts with the hydrogen sulfide to produce a metal sulfide, which is a metal and consequently decreases the energy barrier such that the electrical resistance of the sensing layer 16 measured between the IDEs 14A, 14B decreases. This change in electrical resistivity can be used to indicate the presence of hydrogen sulfide. Further, in an example, the amount of change in electrical resistivity can indicate a concentration of hydrogen sulfide present. The reaction between the p-type metal oxide and the hydrogen sulfide is reversible and, in the absence of hydrogen sulfide, the barrier height increases once again back towards levels approaching or equal to the original barrier height. That is, in the presence of clean air (e.g., absence of hydrogen sulfide) the metal sulfide reverts back to the p-type metal oxide, and the barrier height will increase again to a value specific to the heterostructure between an n-type metal oxide semiconductor and a p-type metal oxide semiconductor.

Figure 2:
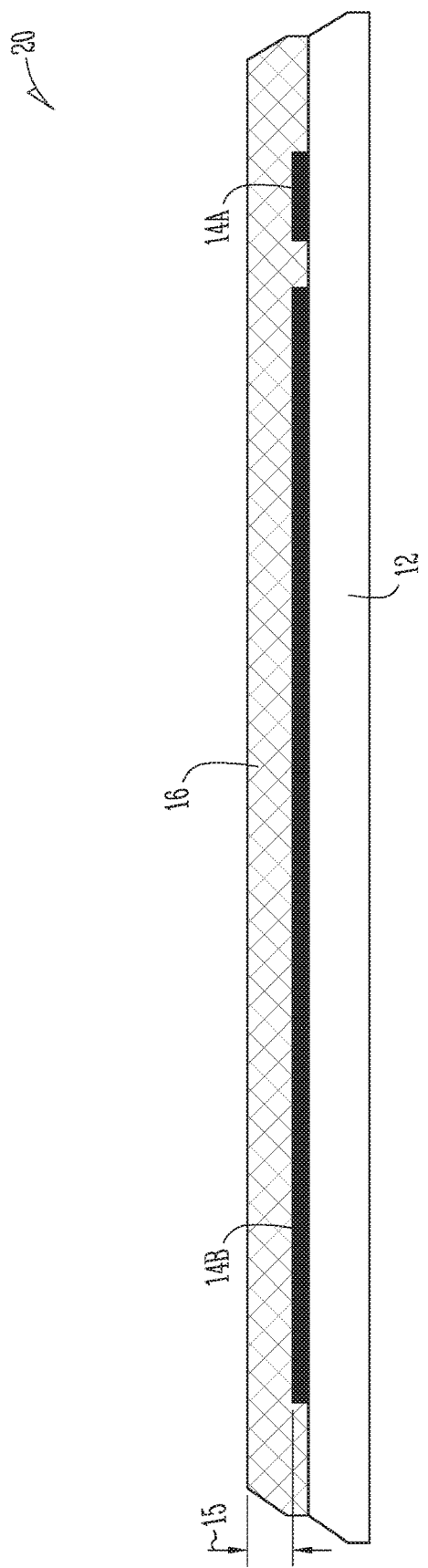
FIG. 2 shows a cross-sectional view of a hydrogen sulfide sensor, in accordance with at least one example

FIG. 2 shows a cross-sectional view 20 of the hydrogen sulfide sensor 10. The hydrogen sulfide sensor can include a substrate 12. Substrate 12 can include the materials described above with respect to substrate 12. Interdigitated electrodes 14A and 14B can be deposited on the substrate 12, such as by a direct printing method. In an example, the sensing layer 16 can be deposited on the IDEs 14A, 14B so as to encompass the IDEs 14A, 14B and form a thin layer above the IDEs 14A, 14B. In an example, a thickness 15 of the layer above the IDEs is about 0.2 μm, 0.4 μm, 0.6 μm, 0.8 μm, 1 μm, 1.2 μm, 1.4 μm, 1.6 μm, 1.8 μm, or 2.0 μm, or 5 μm, or 10 μm or greater. The hydrogen sulfide sensor 10 can include a thin film sensor or a thick film sensor.

In an example, the sensor 10 is configured to detect hydrogen sulfide at temperatures from about 150° C. to about 250° C. The sensor 10 of the present disclosure, including the sensing layer described herein, can cover the domain of sensing hydrogen sulfide at elevated temperatures, while the $H_2S$ sensors based on organic sensing films like polyaniline will be used at temperatures below 60° C.

Figure 3:
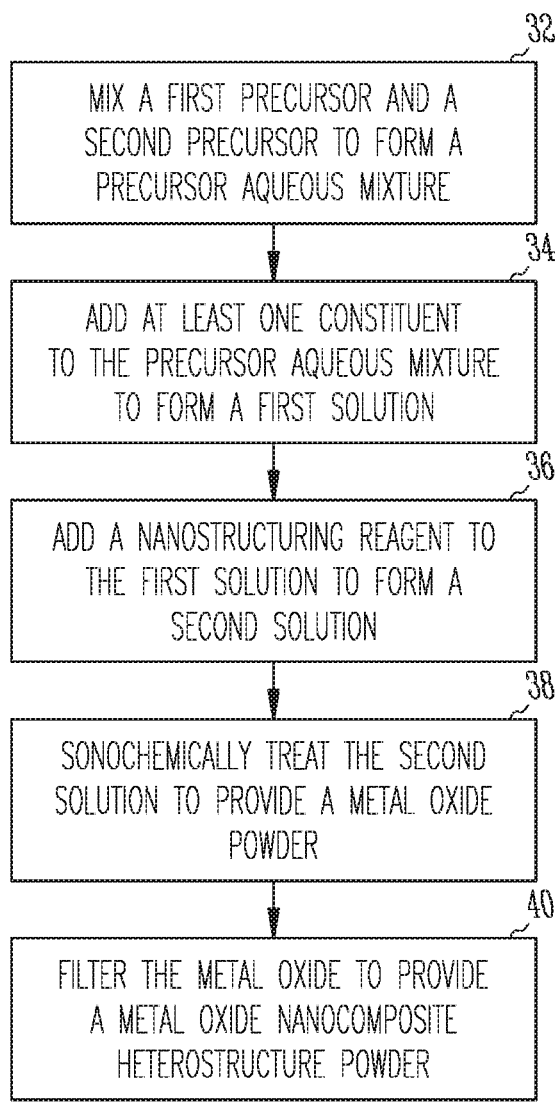
FIG. 3 shows a method of forming a powder of metal oxide nanocomposite heterostructure for a sensing layer of a hydrogen sulfide sensor, in accordance with at least one example.

FIG. 3 illustrates a flow diagram of a sonochemical synthesis method 30 based on aqueous solutions and water/methoxyethanol as a solvent for forming a metal oxide nanocomposite heterostructure powder for a sensing layer of a hydrogen sulfide sensor. The method 30, in an example, can be a batch synthesis process (e.g., one pot synthesis process), as is commonly understood in the art. At 32, the method 30 includes mixing a first precursor and a second precursor to form a precursor aqueous mixture. Mixing can include dissolving the first and second precursors, either separately or together, and combing the dissolved first and second precursors. In an example, the first precursor is used to obtain a p-type semiconducting metal oxide powder and the second precursor is used to obtain an n-type semiconducting metal oxide powder. The first precursor can include at least one metal, such as copper, chromium, and nickel. The second precursor can include at least one metal, such as tin, zinc, molybdenum, and tungsten. In an example, the first and second precursors are selected from a metal oxide, a metal acetate, a metal nitrate, a metal chloride, and a metal isopropoxide, of the metals listed herein. The first and second precursors can include hydrated versions of the base metal oxide, metal acetate, metal acetate, metal chloride, or metal isopropoxide (e.g., zinc nitrate hexahydrate). The precursor aqueous mixture can include a molar ratio of the number of moles of first precursor to the sum of moles of first precursor and second precursor from about 1 mole % to about 30 mole %.

In an example, the method includes adding at least one constituent to the precursor mixture to form a first solution, at 34. In various examples, the at least one constituent can include at least one of a solvent and a reducing agent. In an example including metal isopropoxide precursors the constituent includes two methoxyethanol, but other consitutents, including solvent, like ethanol, can be used. The at least one constituent can include deionized water, sodium hydroxide, acetic acid, and two methoxyethanol. In an example, aqueous synthesis based on metal acetate, nitrate, or chlorides, can include adding the consitutent sodium hydroxide (acting as a reducing agent) as a source of hydroxide anions for the formation of metal oxide powders. The sodium hydroxide (NaOH) can be added in the aqueous solution so that pH of the solution to be in the range of 10-14. In other aqueous synthesis examples, other reducing agent constituent, including urea ($NH_2$—CO—$NH_2$), ammonia ($NH_3$) or hexamethylenetetramine ($(CH_2)_6N_4$), can be used. An advantage of using constituent other than NaOH reducing agents, can include the gradual release of the $OH^-$ anions as a result of the reactions of those agents with water, which may provide a solution with a higher chemical homogeneity. The molar ratio of the water to second metal precursor (giving the n-type metal oxide) is higher than 100, while the molar ratio between metal isopropoxide to two methoxyethanol is about at least about 8 to about 10.

At 36 in, the method 30 includes adding a nanostructuring reagent to the first solution to form a second solution. The molar ratio between the nanostructuring reagent and the second precursor is in from about 1/50 to about 1/70. Examples of the nanostructuring reagent include, but are not limited to, a triblock copolymer, dimethylformamide, P123 Pluronic surfactant, and cetyltrimethyammoniumbromide. The nanostructuring reagent can, in an example, be used to enhance nanostructuring of the heterostructure, as described herein. In an example, for an amount of 2.9 grams of zinc nitrate hexahydrate (about 10 milimoles) the amount of P123 reagent to be added to the solution is equal to about 1 gram. (0.15 milimoles). In an example, more than one nanostructuring reagent can be used.

In an example, the method 30 includes sonochemically treating the second solution to provide a metal oxide powder with the desired stoichiometry of the p-type and n-type oxide components, at 38. Advantages of sonochemically treating the second solution in a batch process can include controlling the level of nanostructuring of the metal oxide powder by varying the levels of power and intensity of the acoustic radiation applied during cavitation-activated chemical reactions between the components of the second solution. The ultrasound power with acoustic waves of a frequency of 24 KHz can be varied in the range of about 50 watts to about 300 watts, and the ultrasound radiation intensity can be in the range of about 130 to about 600 $W/cm^2$. In an example, the metal oxide powder can include the metal oxide nanocomposite heterostructure prior to washing, drying, or filtrating. Sonication, in an example, can include pulsing the second solution with a high acoustic intensity horn at controlled temperatures, from about 1 hour to about 10 hour, and preferably from about 0.5 hours to about 3 hours. In an example, a water cooling system surrounding a reaction beaker can maintain the temperature of the solution remains below 70° C., during high power sonication process. The sonication can be performed at a duty cycle of about 50% to about 100%, and preferably from about 70% to about 100%. During sonication an inert ambient can be kept above the solution, such as an argon flow. The inert ambient can reduce or prevent carbon dioxide from contacting or reacting with the solution, so as to reduce or prevent metal carbonates formation during sonochemical synthesis.

The method 30 can include filtering the metal oxide powder to provide a metal oxide nanocomposite heterostructure, at 40. The metal oxide powder can be separated from the solution by centrifugation for filtering the powder, or by using a filter with a specific porosity. In an the metal oxide can be filtered, washed, and dried to provide a metal oxide nanocomposite heterostructure powder. For example, drying can be under a vacuum at about 80° C. In an example, the metal oxide powder can be washed to provide a metal oxide nanocomposite heterostructure for a sensing layer of a hydrogen sulfide sensor, such as sensor 10, FIG. 1. The metal oxide can be washed in deionized water or deionized water and ethanol until the pH of the solution is neutral. The filtering processes used to extract the powder from the solution can depend on the nature of the solution. In an example where the powder is naturally separated filtering can include repeated washing (adding water and or ethanol to the existing solution and removing a portion of the liquid phase, which may not contain the powder), separation (centrifugation/filtering), and drying the extracted powder. In another example, filtering can include centrifugation, washing and drying.

In an example, the metal oxide nanocomposite heterostructure is tin oxide-copper oxide having a copper oxide molar fraction from about 2 mole % to about 30 mole %. A number of precursors, solvents, and nanostructuring reagents can be used to form the tin oxide-copper oxide nanocomposite heterostructure. An example includes wherein the first precursor is copper chloride, the second precursor is tin chloride, the at least one constituent includes sodium hydroxide, and the nanostructuring reagent includes a triblock copolymer. In another example, the first precursor is copper acetate, the second precursor is tin acetate, and the at least one nanostructuring reagent includes dimethylformamide. In another example, the first precursor is copper isopropoxide, the second precursor is tin isopropoxide, and the at least one constituent includes two methoxyethanol.

In an example, the metal oxide nanocomposite heterostructure is zinc oxide-copper oxide having a copper oxide molar fraction from about 2 mole % to about 30 mole %. A number of precursors, solvents, and nanostructuring reagents can be used to form the zinc oxide-copper oxide nanocomposite heterostructure. An example includes, wherein the first precursor is copper nitrate, the second precursor is zinc nitrate, the at least one constituent is at least one of sodium hydroxide and glucose, and the at least one nanostructuring reagent includes a triblock copolymer. In another example, the first precursor is copper acetate, the second precursor is zinc acetate, and the at least one nanostructuring reagent is dimethylformamide. In another example, the first precursor is copper isopropoxide, the second precursor is zinc isopropoxide, and the at least one constituent includes two methoxyethanol.

In another example, the p-type metal oxide power and the n-type metal oxide powder are pre-formed, such as obtained from a commercial supplier, and mixed in an aqueous solution to which the nanostructuring agent is added, and exposed to the sonochemistry treatment followed by the powder separation (e.g., filtering, washing, and drying) to get the nanocomposite metal oxide heterostructure powder. Such a powder can be further used for the fabrication of the hydrogen sulfide sensor, as discussed herein.

Figure 4:
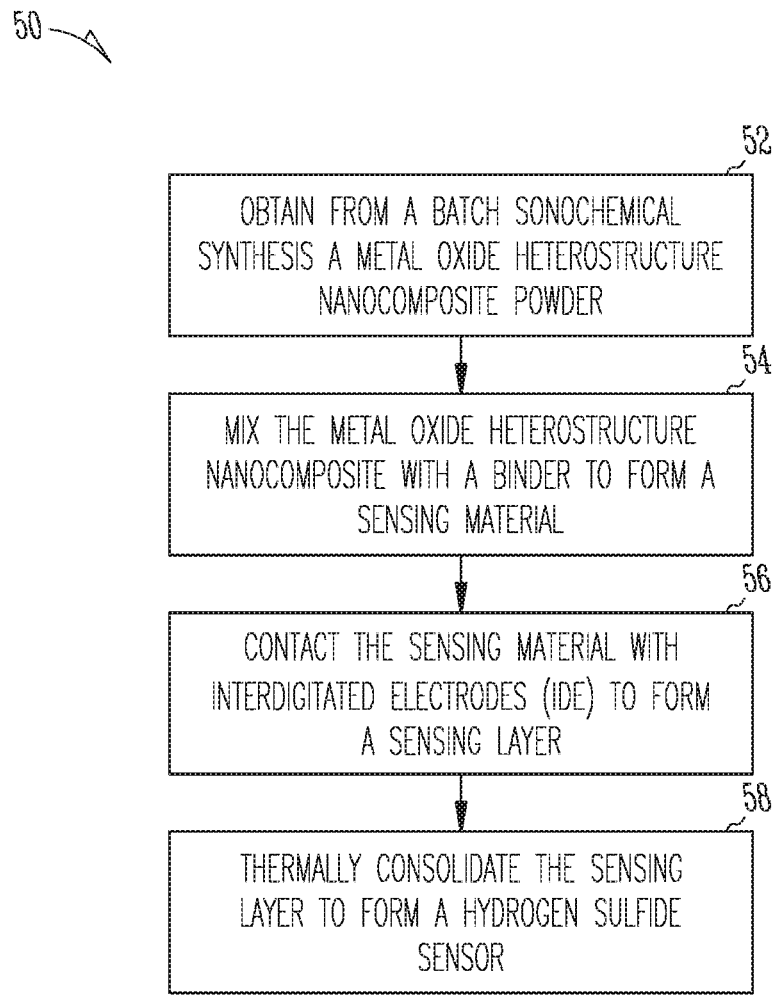
FIG. 4 shows a method of forming a hydrogen sulfide sensor, in accordance with at least one example

FIG. 4 illustrates a flow diagram of a method 50 for forming a hydrogen sulfide sensor including a metal oxide heterostructure nanocomposite. At 52, a metal oxide heterostructure nanocomposite powder is obtained from a batch sonochemical synthesis, as described herein, such as in relation to method 30, FIG. 3. The metal oxide heterostructure nanocomposite can include a metal oxide heterostructure nanocomposite as described herein, such as, for example, in relation to FIG. 1 and FIG. 3. At 54, the metal oxide heterostructure nanocomposite powder is mixed with a binder to form a slurry. The amount of metal oxide heterostructure nanocomposite powder can be from about 0.5 wt % to about 20 wt % of the slurry, depending on the desired thickness of the sensing layer to be formed. In an example, a thick film formation can include a binder such as at least one of terpineol and ethyl cellulose. In an example, a thin film formation can include a binder such as a mixture of water and glycerol, such as about a 10-80 wt % mixture of binder. Further, the thin film formation can include about 0.1wt % to about 10 wt % (of the slurry) of metal oxide powder.

At 56, the method 50 includes contacting the sensing material with interdigitated electrodes (IDEs) to form a sensing layer, such as sensing layer 16, FIG. 1 and FIG. 2. Contacting the slurry sensing material with IDE surface to form the thick sensing layer can include a method, such as screen printing using a shadow mask. Contacting the slurry sensing material with IDE surface to form a thin sensing film can include a method such as maskless direct printing. Alternatively, a thin film can be obtained by spinning the slurry on entire substrate followed by mask-based selective etching of the layer from the regions where the electric contact to the sensor electrodes should be made. At 58, the sensing layer is thermally consolidated to form a hydrogen sulfide sensor, such as sensor 10, FIG. 1. Thermal consolidation can include exposing at least the sensing layer to a temperature at least equal to the ambient temperature during sensor operation, such at about 250° C. to about 450° C. During thermal consolidation, the sensing layer can transform from a gel like, layer obtained during a dropping or spinning process, to a solid state layer to be then used for hydrogen sulfide sensing.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in this document, the terms "first," "second," and "third," etc. are used merely as labels, and are not intended to impose numerical requirements on their objects.

From the foregoing, it will be observed that numerous variations and modifications can be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Although a few embodiments have been described in detail above, other modifications are possible. For example, the logic flows depicted in the FIGS. do not require the particular order shown, or sequential order, to achieve desirable results. Other steps can be provided, or steps can be eliminated, from the described flows, and other components can be added to, or removed from, the described systems. Other embodiments can be within the scope of the following claims.

PROPHETIC EXAMPLES

Prophetic Example 1—Aqueous Synthesis of ZnO—CuO Nanocomposite Heterostructure Powder The method for forming zinc oxide-copper oxide nanocomposite heterostructure powder consisting of 2 mole % of copper oxide in the mixture of zinc oxide (ZnO) and copper oxide (CuO) by an aqueous synthesis, where the aqueous solution is exposed to sonochemical treatment. Mix 0.2 milimoles of Cu $(NO_3)_2 \times 6\ H_2O$ (0.04832 grams) with 9.8 milimoles of $Zn(NO_3)_2 \times 3H_2O$ (2.915402 grams). Dissolve the mixture in 60 ml of water while stirring. Add a reducing agent (to get a concentration from 0.5 molar to about 4 molar in the first solution) and a nanostructuring reagent (from 0.1 to 1 milimole) to the first solution. Sonochemically treat the second solution for about 0.5-3 hours, at an ultrasound power of 50-300 W and ultrasound power intensity of 130-600 W/cm$^2$ to provide a nanocomposite metal oxide heterostructure. Filter and wash the nanocomposite metal oxide heterostructure. Dry the metal oxide powder in a vacuum at 80° C.

Prophetic Example 2 —Aqueous Synthesis of $SnO_2$—CuO Nanocomposite Heterostructure Powder The method for forming $SnO_2$—CuO nanocomposite heterostructure powder with 5% mole percent of CuO oxide in the mixture of tin dioxide by an aqueous synthesis, where the organic precursors are exposed to the sonochemical treatment. Dissolve 0.5 milimoles of copper isopropoxide (0.091 grams) in 10 ml of two-methoxyethanol. Dissolve 9.5 milimoles of tin isopropoxide (3.373 grams) in 30 ml of two-methoxyethanol. Mix the two solutions, while stirring, and add 5 milimoles of acetic acid (0.3 grams) and nanostructuring agent (0.1 milimoles to 1 milimole (0.58 grams to 5.8 grams)). Add 30 ml of water drop wise to the solution from the previous step. Expose the solution to ultrasound treatment for 0.5-3 hours with acoustic waves of 24 KHz, power of 50-300 W, and intensity of 130-600 cm$^2$ to provide a nanocomposite metal oxide heterostructure. Filter and wash the nanocomposite metal oxide heterostructure extracted from the sonochemically treated solution by centrifugation. Dry the metal oxide powder. It can be done in vacuum at 80° C.

EXAMPLES

Examples of the present disclosure provide hydrogen sulfide sensors including a sensing layer having a metal oxide nanocomposite heterostrcuture and methods of forming the metal oxide nanocomposite heterostrcuture.

Example 1 includes subject matter directed toward a method for forming a metal oxide nanocomposite heterostructure powder for a sensing layer of a hydrogen sulfide sensor, comprising: mixing a first precursor and a second precursor to form a precursor aqueous mixture; adding at least one constituent to the precursor aqueous mixture to form a first solution; adding at least one nanostructuring reagent to the first solution to form a second solution; sonochemically treating the second solution to provide a metal oxide powder; filtering the metal oxide powder to provide a metal oxide nanocomposite heterostructure powder for a sensing layer of a hydrogen sulfide sensor.

In Example 2, the subject matter of Example 1 can be optionally configured wherein the first precursor is a precursor for a p-type metal oxide and the second precursor is a precursor for a n-type metal oxide and each of the first and second precursors is selected from the group consisting of a metal oxide, a metal acetate, a metal nitrate, a metal chloride, and a metal isopropoxide.

In Example 3, the subject matter of Examples 1 or 2 can be optionally configured wherein the metal oxide nanocomposite heterostructure is tin oxide-copper oxide having a copper oxide molar fraction from about 2 mole percent to about 30 mole percent.

In Example 4, the subject matter of Examples 1-3 can be optionally configured wherein: the first precursor is copper chloride and the second precursor is tin chloride, the at least one constituent includes sodium hydroxide, and the at least one nanostructuring reagent includes a triblock copolymer.

In Example 5, the subject matter of Examples 1-4 can be optionally configured wherein: the first precursor is copper acetate and the second precursor is tin acetate, and the at least one nanostructuring reagent includes dimethylformamide.

In Example 6, the subject matter of Examples 1-5 can be optionally configured wherein: the first precursor is copper isopropoxide and the second precursor is tin isopropoxide, and the at least one constituent includes two methoxyethanol.

In Example 7, the subject matter of Examples 1-6 can be optionally configured wherein the metal oxide nanocomposite heterostructure is zinc oxide-copper oxide having a copper oxide molar fraction from about 2 mole percent to about 30 mole percent.

In Example 8, the subject matter of Examples 1-7 can be optionally configured such that wherein: the first precursor is copper nitrate and the second precursor is zinc nitrate, the at least one constituent includes at least one of sodium hydroxide and glucose, and the at least one nanostructuring reagent includes a triblock copolymer.

In Example 9 the subject matter of Examples 1-8 can be optionally configured wherein: the first precursor is copper acetate and the second precursor is zinc acetate, and the at least one nanostructuring reagent includes dimethylformamide.

In Example 10, the subject matter of Examples 1-9 can be optionally configured such that wherein: the first precursor is copper isopropoxide and the second precursor is zinc isopropoxide, and the at least one constituent includes two methoxyethanol.

Example 11, includes subject matter directed to a method of forming a hydrogen sulfide sensor including a metal oxide heteroxtructure nanocomposite, comprising: obtaining, from a batch sonochemical synthesis, a metal oxide heterostructure nanocomposite powder; mixing the metal oxide heterostructure nanocomposite powder with a binder to form a sensing material; contacting the sensing material with interdigitated electrodes (IDE) to form a sensing layer; and thermally consolidating the sensing layer to form a hydrogen sulfide sensor.

In Example 12, the subject matter of Examples 1-11 can be optionally configured such that wherein the metal oxide heterostructure nanocomposite is selected from the group consisting of $MoO_3$—CuO, $SnO_2$—CuO, and ZnO—CuO, $SnO_2$—NiO, $SnO_2$—$Cr_2O_3$, ZnO—NiO, ZnO—$Cr_2O_3$, and $MoO_3$—NiO.

In Example 13, the subject matter of Examples 1-12 can be optionally configured such that wherein depositing includes depositing the sensing material maskless or through a shadow mask.

In Example 14, the subject matter of Examples 1-13 can be optionally configured such that wherein the binder includes at least one of terpineol, glycerol, and water.

Example 15 includes subject matter directed to a method of forming a hydrogen sulfide sensor including a metal oxide heteroxtructure nanocomposite, comprising: obtaining p-type metal oxide powder and an n-type metal oxide powder; mixing, in an aqueous solution, the p-type metal oxide powder and the n-type metal oxide powder to for a solution; adding a nanostructuring agent to the solution; sonochemically treating the second solution to provide a metal oxide powder; filtering the metal oxide powder; washing the metal oxide powder; and drying the metal oxide powder to provide a metal oxide nanocomposite heterostructure powder for a sensing layer of a hydrogen sulfide sensor.

What is claimed is:

1. A method of forming a hydrogen sulfide sensor including a metal oxide heterostructure nanocomposite, comprising:
    obtaining, from a batch sonochemical synthesis, a metal oxide heterostructure nanocomposite powder formed by sonochemically treating a solution of p-type metal oxide precursor, n-type metal oxide precursor, and a nanostructuring agent,
    wherein the sonochemical treatment includes controlling a level of nanostructuring of the metal oxide heterostructure nanocomposite powder by varying levels of power and intensity of an acoustic radiation between components of the solution;
    mixing the metal oxide heterostructure nanocomposite powder with a binder to form a sensing material;
    depositing the sensing material with interdigitated electrodes (IDE) onto a surface of a substrate to form a sensing layer; and
    thermally consolidating the sensing layer to form a hydrogen sulfide sensor.

2. The method of claim 1, wherein the metal oxide heterostructure nanocomposite is selected from the group consisting of $MoO_3$—CuO, $SnO_2$—CuO, and ZnO—CuO, $SnO_2$—NiO, $SnO_2$—$Cr_2O_3$, ZnO—NiO, ZnO—$Cr_2O_3$, and $MoO_3$—NiO.

3. The method of claim 1, wherein depositing includes depositing the sensing material maskless or through a shadow mask.

4. The method of claim 1, wherein the binder includes at least one of terpineol, glycerol, and water.

5. The method of claim 1, wherein the nanostructuring agent comprises a triblock copolymer, dimethylformamide, P123 Pluronic surfactant, cetyltimethyammoniumbromide, or combinations thereof.

6. A method of forming a hydrogen sulfide sensor including a metal oxide heterostructure nanocomposite, comprising:
    obtaining p-type metal oxide powder and an n-type metal oxide powder;
    mixing, in an aqueous solution, the p-type metal oxide powder and the n-type metal oxide powder to form a solution;
    adding a nanostructuring agent to the solution;
    after adding the nanostructuring agent to the solution, sonochemically treating the solution to provide a metal oxide powder,
    wherein the sonochemical treatment includes controlling a level of nanostructuring of the metal oxide heterostructure nanocomposite by varying levels of power and intensity of an acoustic radiation between components of the solution;
    filtering the metal oxide powder;
    washing the metal oxide powder; and
    drying the metal oxide powder to provide a metal oxide nanocomposite heterostructure powder for a sensing layer of a hydrogen sulfide sensor.

7. The method of claim 6, wherein the metal oxide heterostructure nanocomposite is selected from the group consisting of $MoO_3$—CuO, $SnO_2$—CuO, and ZnO—CuO, $SnO_2$—NiO, $SnO_2$—$Cr_2O_3$, ZnO—NiO, ZnO—$Cr_2O_3$, and $MoO_3$—NiO.

8. The method of claim 6, wherein obtaining p-type metal oxide powder and an n-type metal oxide powder, includes:
    mixing a first precursor and a second precursor to form a precursor aqueous mixture, wherein the first precursor is a precursor for a p-type metal oxide and the second precursor is a precursor for a n-type metal oxide.

9. The method of claim 8, wherein the first precursor and the second precursor are selected from the group consisting of a metal oxide, a metal acetate, a metal nitrate, a metal chloride, and a metal isopropoxide.

10. The method of claim 6, further including:
    mixing the metal oxide heterostructure nanocomposite powder with a binder to form a sensing material;
    depositing the sensing material with interdigitated electrodes (IDE) onto a surface of a substrate to form a sensing layer; and
    thermally consolidating the sensing layer to form a hydrogen sulfide sensor.

11. The method of claim 10, wherein depositing includes depositing the sensing material maskless or through a shadow mask.

12. The method of claim 6, wherein the nanostructuring agent comprises a triblock copolymer, dimethylformamide, P123 Pluronic surfactant, cetyltrimethyammoniumbromide, or combination thereof.

* * * * *